(12) United States Patent
Hempstead

(10) Patent No.: US 8,009,279 B2
(45) Date of Patent: Aug. 30, 2011

(54) CHARACTERIZATION OF NON-LINEAR OPTICAL MATERIALS USING BRAGG COUPLING

(75) Inventor: Martin Hempstead, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 426 days.

(21) Appl. No.: 12/352,175

(22) Filed: Jan. 12, 2009

(65) Prior Publication Data

US 2010/0177301 A1 Jul. 15, 2010

(51) Int. Cl.
*G01N 21/00* (2006.01)
(52) U.S. Cl. ...................................................... 356/73.1
(58) Field of Classification Search .................. None
See application file for complete search history.

(56) References Cited

U.S. PATENT DOCUMENTS

| 5,781,670 | A | 7/1998 | Deacon et al. | |
|---|---|---|---|---|
| RE37,809 | E | * 7/2002 | Deacon et al. | 372/102 |
| 6,834,151 | B1 | 12/2004 | Smith et al. | |
| 7,062,131 | B2 | 6/2006 | Ilchenko | |
| 7,236,674 | B2 | 6/2007 | Mizuuchi et al. | |
| 2003/0231302 | A1 | 12/2003 | Hunt | |
| 2006/0044641 | A1 | 3/2006 | Alles et al. | |
| 2006/0233206 | A1 | 10/2006 | Miner et al. | |
| 2006/0257084 | A1 | 11/2006 | Mizuuchi et al. | |

FOREIGN PATENT DOCUMENTS

| WO | 02/31591 A1 | 4/2002 |
|---|---|---|
| WO | 2005008296 A2 | 1/2005 |

OTHER PUBLICATIONS

"Electrically induced Bragg-diffraction granting composed of periodically inverted domains in lithium niobate crystals and its application devices"; Yamada; Review of Scientific Instruments; vol. 71, No. 11, Nov. 2000.
"Demonstration and optical characteristics of elecro-optic Bragg modulators in periodically poled lithium niobate in the near-infrared"; Abernethy et al.; Applied Physics Letters; vol. 81, No. 14, Sep. 2002.
"High conversion efficiency single-pass second harmonic generation in a zinc diffused periodically poled lithium niobate waveguide"; Ming et al.; Optic Express, vol. 13, No. 13, Jun. 2005.

* cited by examiner

*Primary Examiner* — Tu Nguyen
(74) *Attorney, Agent, or Firm* — Knadjo Adusei-Poku

(57) ABSTRACT

Methods of characterizing non-linear optical materials and fabricating wavelength conversion devices are provided. The method of characterizing non-linear optical materials comprising a periodically poled waveguide layer and at least one waveguide region includes coupling at least one diagnostic laser beam into the waveguide region at one or more input locations positioned on the waveguide layer of the non-linear optical material, and out-coupling the diagnostic laser beam from the waveguide region by applying an electric field to the periodically poled domains at one or more output locations positioned on the waveguide layer. The method also includes measuring an intensity level of the out-coupled beam and determining at least one optical property of the waveguide region based at least in part on the measured intensity level of the out-coupled beam. The characterization method may be implemented into a wavelength conversion fabrication process.

16 Claims, 2 Drawing Sheets

CHARACTERIZATION OF NON-LINEAR OPTICAL MATERIALS USING BRAGG COUPLING

BACKGROUND

1. Field

Embodiments of the present invention relate to the characterization of non-linear optical materials. More specifically, embodiments of the present invention relate to using Bragg coupling to determine optical properties of waveguide regions of non-linear optical materials.

2. Technical Background

Non-linear optical materials such as non-linear optical crystals may be utilized in optical systems to generate higher harmonic waves of a fundamental laser signal. For example and by way of illustration, not limitation, short wavelength sources may be configured for high-speed modulation by combining a single-wavelength semiconductor laser, such as a distributed feedback (DFB) laser, a distributed Bragg reflector (DBR) laser, a vertical cavity surface-emitting laser (VCSEL), a vertical external cavity surface-emitting laser (VECSEL), or a Fabry-Perot laser, for example, with a light wavelength conversion device, such as a second harmonic generation (SHG) crystal or a higher harmonic generating crystal. SHG crystals use second harmonic generation properties of non-linear crystals to frequency-double laser radiation. For example, a SHG crystal may be configured to generate green light by converting the wavelength of a 1060 nm DBR or DFB laser to 530 nm.

In many applications, such as laser projection systems, optical properties of the wavelength conversion device are critical to system performance. Particular optical properties may include propagation loss, peak conversion wavelength and optical power conversion efficiency, among others. For example, the conversion efficiency of a SHG crystal, such as MgO-doped periodically poled lithium niobate (PPLN), is strongly dependent on the wavelength matching between the laser diode and the SHG device. The bandwidth of a PPLN SHG device is often very small—for a typical PPLN SHG wavelength conversion device, the full-width half-maximum (FWHM) wavelength conversion bandwidth is only in the 0.16 to 0.2 nm range and mostly depends on the length of the crystal. Once the semiconductor laser wavelength deviates outside the wavelength conversion bandwidth of the PPLN SHG device, the output power of the conversion device at the target wavelength drops.

Wavelength conversion devices such as PPLN SHG devices are often fabricated from a wafer of a non-linear material such as lithium niobate or lithium tantalate that may contain a plurality of wavelength conversion devices defined by a plurality of waveguide regions to be diced from the wafer. The wafer comprises a waveguide layer of periodically poled non-linear material that is adhered to a substrate. The waveguide layer may be periodically poled by applying a voltage to a pattern that is applied to the wafer via photolithography, for example. The conversion center wavelength is determined by the period of the poling as well as by the details of the waveguide geometry and index distribution. The tolerance requirements may be very demanding. Some waveguides may fall outside of the acceptable tolerance such that further processing of these waveguides is undesirable.

Although wavelength conversion devices must meet strict tolerance requirements, current mass production methods do not provide for the testing or characterization of wavelength conversion devices during the fabrication process. As such, the devices are commonly tested after fabrication is completed. For example, testing methodologies require injecting light into and extracting it from the endfaces of the wavelength conversion devices after the dicing and endface polishing of the individual wavelength conversion devices from the wafer. Further, current methods do not allow the many waveguide regions of the wafer to be tested concurrently.

Testing SHG devices and rejecting failures after fabrication results in wasted resources and production time. If defects in a portion or portions of the wafer could be detected early in the fabrication process, the defective portions could be discarded. Further processing may then be limited to those portions that meet the optical properties or requirements, thereby decreasing processing costs and increasing production yield.

BRIEF SUMMARY

It is against this background that methods of characterizing of non-linear optical waveguides during fabrication are desired.

According to one embodiment, a method of characterizing a non-linear optical material comprising a periodically poled waveguide layer and at least one waveguide region therein is disclosed. The method includes coupling at least one diagnostic laser beam into the waveguide region at one or more input locations positioned on the waveguide layer of the non-linear optical material, and out-coupling the diagnostic laser beam from the waveguide region by applying an electric field to the periodically poled domains at one or more output locations positioned on the waveguide layer. The method also includes measuring an intensity level of the out-coupled beam and determining at least one optical property of the waveguide region based at least in part on the measured intensity level of the out-coupled beam.

According to another embodiment, a method of fabricating a wavelength conversion device from a non-linear optical material comprising a periodically poled waveguide layer and at least one waveguide region therein is disclosed. The method includes coupling at least one diagnostic laser beam into the waveguide region at one or more input locations positioned on the waveguide layer, and out-coupling the diagnostic laser beam from the at least one waveguide region by applying an electric field to the periodically poled domains at one or more output locations positioned on the waveguide layer. The method further includes measuring an intensity level of the out-coupled beam, determining at least one optical property of the waveguide region based at least in part on the measured intensity level of the out-coupled beam, and characterizing at least a portion of the non-linear optical material for further processing based at least in part on the at least one optical property of the waveguide region.

BRIEF DESCRIPTION OF THE SEVERAL VIEWS OF THE DRAWINGS

The following detailed description of specific embodiments of the present invention may be best understood when read in conjunction with the following drawings, where like structure is indicated with like reference numerals and in which.

DETAILED DESCRIPTION

Embodiments of the present disclosure allow optical characterization and testing of non-linear optical materials (e.g., second harmonic generation crystals ("SHGs")) prior to dicing and endface polishing, and without the need for coupling prisms or fabrication of specific coupling structures such as Bragg gratings (although embodiments of the present disclosure may be utilized in conjunction with such prisms and structures). As described in detail herein below, embodiments utilize coupling methods that use the inherent physical properties of non-linear optical materials to control input and output coupling for waveguide characterization. Light is coupled into a non-linear optical material along a waveguide layer at an input location and then out-coupled at an output location where it is measured and optical properties of the non-linear optical material are determined.

Although the specific structure of the various types of wavelength conversion devices (such as SHG crystals) in which the concepts of particular embodiments of the present disclosure can be incorporated is taught in readily available technical literature relating to the design and fabrication of wavelength conversion devices, the concepts of particular embodiments of the present disclosure maybe conveniently illustrated with general reference to periodically poled lithium niobate crystals (PPLN). It is noted that embodiments may also be utilized to test non-linear optical materials other than PPLN, such as periodically poled lithium tantalate (PPLT), potassium titanyl phosphate (KTP) and others.

Figure 1A:
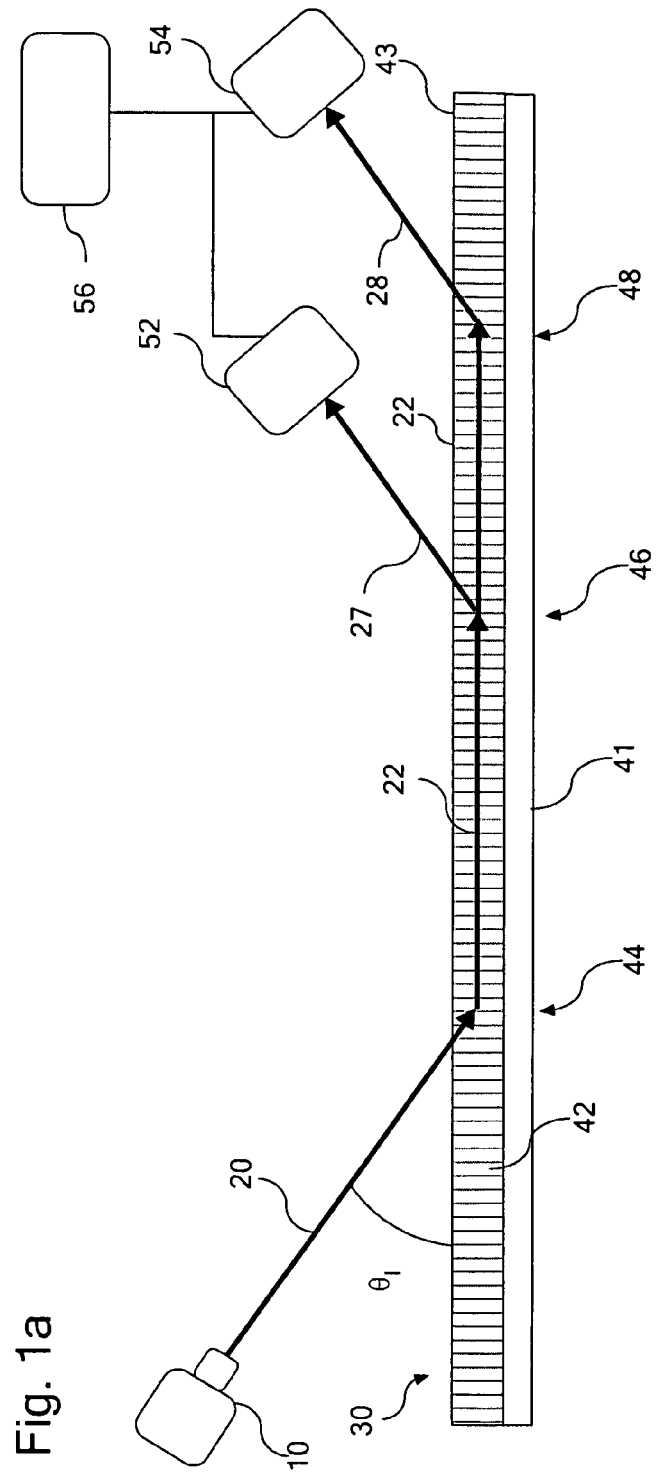
FIG. 1a is a schematic illustration of an exemplary diagnostic laser beam coupled into and out of a waveguide region of a non-linear optical material according to one or more embodiments.
Figure 2:
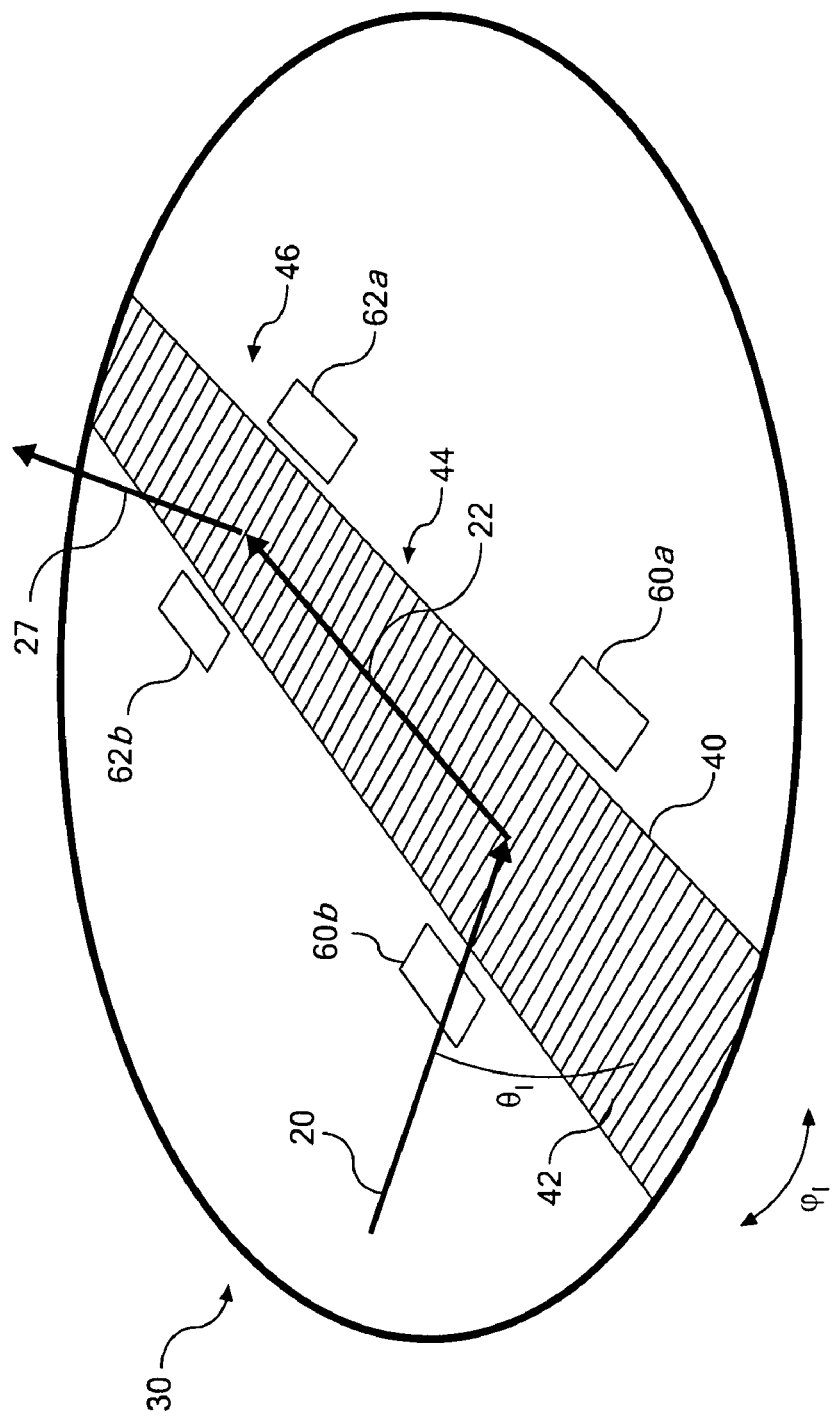
FIG. 2 is a schematic illustration of an exemplary diagnostic laser beam coupled into and out of a waveguide region of a non-linear optical material according to one or more embodiments.

FIGS. 1a and 2 illustrate a non-linear optical material characterization method according to one embodiment. FIG. 1a illustrates a profile view of a waveguide layer 43 positioned on a substrate 41, such as a lithium niobate substrate, for example. FIG. 2 illustrates a single waveguide region 40 within a wafer 30. Although FIG. 2 illustrates only a single waveguide region 40, a wafer 30 may comprise many waveguide regions 40 that may be tested according to embodiments disclosed herein. Lateral confinement of waveguide regions 40 within the wafer 30 may be created by laser ablation, for example. The term waveguide region means the region of the waveguide layer in which the beam propagates and may be a laterally defined region if the characterization is performed after laser ablation or an undefined region within the waveguide layer if the characterization is performed prior to laser ablation. The illustrated waveguide layer 43 and regions 40 of FIGS. 1a and 2 comprise a plurality of periodically poled domains 42. The individual waveguide regions 40 may be diced and polished to fabricate a plurality of wavelength conversion devices from a single wafer 30.

According to the illustrated embodiment, a diagnostic laser beam 20 is generated by a laser source 10 (FIG. 1a) and coupled into the waveguide region 40 of the waveguide layer 43 at an input location 44. According to some embodiments, the laser source 10 may be configured to generate an infrared diagnostic laser beam 20. Additionally, the laser source 10 may be configured to sweep a range of wavelengths, and also adjust the angle of incidence of the diagnostic laser beam 20 upon the wafer 30. Input electrodes 60a and 60b (FIG. 2) may be utilized to apply an electric field on the surface of the wafer to further enhance coupling of the diagnostic laser beam 20. A coupled portion of the diagnostic laser beam 22 then propagates within the waveguide region 40. Electrodes (e.g., 62a and 62b of FIG. 2) may also be utilized to control the out-coupling of the guided beam 22 at output locations 46 and 48.

Output detectors such as 52 and 54 maybe located at output locations (e.g., 44 and 46 of FIG. 1a) to detect an intensity level of the out-coupled beam 27, 28. The output detectors 52 and 54 may be configured as photodiodes or other similar devices capable of measuring the power of the out-coupled beam 27, 28. According to the illustrated embodiment, the output detectors 52 and 54 are coupled to a microcontroller or computer 56. The microcontroller or computer 56 may be configured to compare the measured intensity level of the out-coupled beam 27, 28 to a standard value or threshold, display the measured intensity level, or instruct an automated process to take action depending on the measured intensity level. Other embodiments may not utilize a microcontroller or computer 56. For example, the detector may provide a read-out of the detected intensity level and further action may be taken based on the provided read-out.

Unlike conventional testing methods, embodiments of the present disclosure provide methods for coupling light into and out of non-linear optical material wafers before individual waveguide regions are diced from the wafer. Referring to FIG. 1a, a diagnostic laser beam 20 may be injected into one or more waveguide regions 40 at an input angle $\theta_I$. Rather than coupling light into the waveguide region 40 via the fabrication of Bragg gratings or use of coupling prisms, the periodically poled region of the waveguide region 40 is used as an intrinsic Bragg grating to couple free-space radiation into and out of guided radiation within the waveguide region 40. The Bragg grating is the intrinsic grating that forms in a parasitic fashion when the periodically poled structure is created. Embodiments exploit the intrinsic index gratings in PPLN (or other non-linear optical materials) to couple light into and out of the waveguide region or regions 40 without the use of additional coupling devices or gratings.

According to some embodiments, the intrinsic Bragg grating of the PPLN structure may be enhanced and controlled by the application of an electric field on the surface of the wafer 30. The electroopic effect that aids in-coupling and out-coupling of the light may be achieved by applying voltage to electrodes (e.g., electrodes 60a, 60b and 62a, 62b illustrated in FIG. 2) positioned on the surface of the waveguide region 40. The electrodes may be applied at various points on the waveguide layer 43 during the fabrication process, and may be patterned such that different regions of the wafer may be used as points for in-coupling and out-coupling.

As lithium niobate is an electrooptic material, an electric field applied in the region of the poled domains such that a component of the field is aligned with the crystal polar axis will enhance the index modulation depth and thereby strengthen the coupling. Referring to FIG. 2, input electrodes 60a and 60b may be placed at a desired input location 44 along a waveguide region 40 to be tested. The electrodes 60a and 60b may be patterned to strengthen coupling of the diagnostic laser beam 20 into the waveguide region 40 when current or voltage is applied thereto. According to other embodiments, electrodes are not used for input coupling.

Similarly, output electrodes 62a and 62b may be applied along the waveguide region 40 at a desired output location 46 (or locations). The output electrodes 62a and 62b allow the guided beam 22 to be out-coupled in a controlled manner at selected output locations. Any number of output electrodes may be applied along the waveguide region to provide multiple output locations. The input and output electrodes may be controlled by a microcontroller or a computer 56, or any control method that allows the electrodes to be selectively controlled.

Figure 1B:
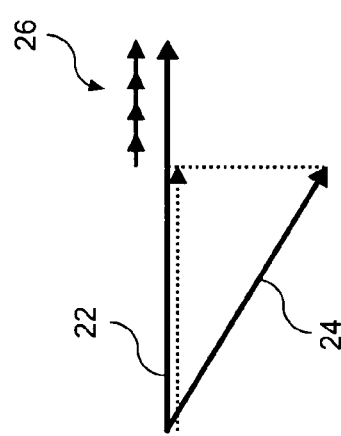
FIG. 1b is a schematic illustration of guided and unguided k-vectors of a diagnostic laser beam according to one or more embodiments.

FIG. 1b is a schematic representation of the coupling of a diagnostic laser beam 20 into the waveguide region 40, which involves a change in wavevector or momentum as the diagnostic laser beam 20 traverses from free space into the waveguide region 40. The periodic index structure of the periodically poled regions 42 provides a means for wavevector or momentum matching. The grating period of the waveguide region 40 is equal to the poling period of the periodically poled domains 42.

Only k-vector components of the guided beam 22 along the waveguide region 40 need to be matched. The perpendicular component is matched by high spatial frequency components of the structure. Multiple orders k (illustrated as 26 in FIG. 2) of the index grating vector compensate the mismatch in the unguided and guided k-vectors. The number of orders k required for coupling is determined by taking the difference between the projection of the k-vector of the free-space wave 20 in the direction of the waveguide region 40 and the k-vector of the guided mode 22 divided by the k-vector of the index grating. Therefore, if the diagnostic laser beam 20 is projected into the waveguide region 40 at an input angle $\theta_I$ as illustrated in FIG. 1, the number of orders required for coupling may be defined by:

$$k = \frac{\Lambda(\eta_{\mathit{eff}} - \cos(\theta_I))}{\lambda_{vac}}, \quad (1)$$

where:
$\Lambda$ is the poling or grating period of the waveguide region 40;
$\eta_{\mathit{eff}}$ is the effective index of the waveguide region 40 at the wavelength of the diagnostic laser beam;
$\theta_I$ is the input angle of the diagnostic laser beam 20; and
$\lambda_{vac}$ is the wavelength of the diagnostic laser beam 20 in a vacuum.

As an example and not a limitation, given the index difference between air and lithium niobate, ~1 and ~2.2 respectively, and the period of a PPLN of about 6.6 μm, coupling requires at least 8 orders for infrared wavelength and at least 15 orders for the wavelength-converted beam (4 orders are shown in the diagram). If the index modulation is a boxcar function, then only odd orders will have non-zero coupling, so the minimum for IR is 9. The strength of the coupling for the odd orders is inversely proportional to the square of the number of orders in this case. It is noted that the diagnostic wavelength may be different from the use wavelengths. The term use wavelength may be defined as the wavelength or wavelengths of the input laser or lasers used in the application of the wavelength conversion device, such as use in a laser projection device, for example.

According to another embodiment, dedicated coupling sections may be introduced into the waveguide layer 43 or particular waveguide regions 40 during the poling process by making the poling period different in these sections than the poling period elsewhere in the waveguide. For example, decreasing the poling period in the coupling sections enhances coupling and allows for larger coupling angles while not significantly impacting the conversion efficiency of the wavelength conversion device.

Embodiments of the present invention may utilize the above-described coupling methods to characterize portions of a non-linear optical material wafer 30 according to optical properties such as propagation loss, center wavelength (i.e., the peak conversion wavelength) and conversion efficiency. Individual wavelength conversion devices may also be tested using the described coupling methods. These optical properties may be determined during the manufacturing process or after fabrication, if desired. Undiced wafers 30 or portions of the wafers may be assigned for further processing or rejection depending on the results of the characterization.

Propagation loss within portions of the waveguide region 40 or regions 40 maybe measured by selecting one or more fixed input locations 44 and sequentially activating electrodes at two or more output locations along the waveguide region 40 that is to be tested, as illustrated in FIGS. 1a and 2. Referring to FIG. 1a, the coupled beam 22 traveling within the waveguide region 40 is out-coupled at output location 46 as electrodes 62a and 62b are turned on. Output detector 52 measures the power of the out-coupled beam 27. According to some embodiments, the measurement result is sent to the microcontroller or computer 56 for processing. The result may be sent to the microcontroller or computer 56 by a wireless or wired communication link, for example. The electrodes 62a and 62b at output location 46 may then be turned off and electrodes at output location 48 (these electrodes not shown) turned on. The coupled beam 22 now travels within the waveguide region 40 from input location 44 to a second output location 48, where it is out-coupled via a second applied electric field. Output detector 54 measures the power of the out-coupled beam 28 at the second output location and may then send the result to the microcontroller or computer 56. It is noted that other detection configurations are possible. For example, some embodiments may utilize a single detector that is capable of detecting both of the out-coupled beams 27, 28. Other embodiments may not utilize a microcontroller or computer 56.

The propagation loss within the waveguide region 40 between output locations 46 and 48 may be determined by taking the difference between the measured power of the out-coupled beams at output locations 46 and 48. If the propagation loss is not within a tolerance (e.g., it is above a threshold level or standard value), the waveguide region 40 may be marked or flagged for rejection and further processing may be ceased as to the failed waveguide region or regions 40.

The center wavelength $\lambda_{cw}$ of the waveguide region or regions 40 within a wafer 30 may also be measured. Because the poling period $\Lambda$ is determined by the photolithographic process described above and is therefore known, the center wavelength $\lambda_{cw}$ of the waveguide region 40 may be determined by its effective index $\eta_{\mathit{eff}}$ at the wavelength of the diagnostic laser beam 20, which may be determined by:

$$\eta_{\mathit{eff}} = \frac{k \cdot \lambda_{vac}}{\Lambda} + \cos(\theta_{OI}), \quad (2)$$

where:
$\theta_{OI}$ is the optimal input angle of the diagnostic laser beam 20; and
k is the number of orders required for coupling.

The effective index $\eta_{\mathit{eff}}$ of the waveguide region 40 may be determined by altering variables in equation (2) above. According to one embodiment, the poling period $\Lambda$, the number of orders k, and the wavelength of the diagnostic laser beam $\lambda_{vac}$ are known and fixed during the test. The laser source 10 may be controlled such that the input angle $\theta_I$ of the diagnostic laser beam 20 is adjusted in order to determine the optimal input angle $\theta_{OI}$. As the input angle $\theta_I$ is adjusted, the intensity of the out-coupled beam (e.g., beam 27) is measured. The optimal input angle $\theta_{OI}$ is the input angle $\theta_I$ that yields the highest measured intensity level of the out-coupled beam 27. The optimal input angle $\theta_{OI}$ may then be used to determine the effective index $\eta_{eff}$ at the wavelength of the diagnostic laser beam 20, which may be in the infrared band according to some embodiments.

Having determined the effective index $\eta_{eff}$ of the waveguide region 40 at the diagnostic wavelength $\lambda_{vac}$ and knowing the poling period $\Lambda$ of the waveguide region 40, the center wavelength $\lambda_{cw}$ of the waveguide region 40 may be determined by:

$$\lambda_{cw} = 2\Lambda(\eta_{2\upsilon} - \eta_{eff}), \quad (3)$$

where $\eta_{2\upsilon}$ is the effective index of the waveguide region 40 at the converted wavelength of the diagnostic laser beam.

Because the effective index at the converted wavelength $\eta_{2\upsilon}$ is closely correlated with the effective index at the diagnostic wavelength $\eta_{eff}$, the effective index at the converted wavelength $\eta_{2\upsilon}$ may be inferred from the effective index at the diagnostic wavelength $\eta_{eff}$. For example, $\eta_{2\upsilon}$ may be determined by utilizing a lookup table, past waveguide characterizations or modeling based on the determined effective index $\eta_{eff}$. Additionally, the center wavelength $\lambda_{cw}$ may be obtained by use of a lookup table or model. The determined center wavelength $\lambda_{cw}$ may then be compared to a threshold value or a tolerance range. If the center wavelength $\lambda_{cw}$ is outside of the tolerance range, the waveguide region 40 may then be marked or flagged as rejected. A similar approach may be used if the effective index is measured at a non-use wavelength.

Other embodiments may adjust the relative position of the wafer 30 rather than adjusting the angle of the diagnostic laser beam 20. For example, the wafer 30 may be tilted up and down to vary the relative input angle $\theta_I$. The center wavelength $\lambda_{cw}$ may then be determined as described above. Alternatively, as illustrated in FIG. 2, the input angle $\theta_I$ may remain fixed and the wafer 30 rotated about a center point to adjust an input azimuthal angle $\phi_I$ (see FIG. 2) wherein the fixed input angle $\theta_I$ is the polar angle. Angle $\phi_I$ may be adjusted while measuring the intensity level of the out-coupled beam via a detector (e.g., detector 52) to determine the optimal azimuthal angle $\phi_{OI}$ that yields the highest measured intensity level. The effective index at the diagnostic wavelength $\eta_{eff}$ may be determined by:

$$\eta_{eff} = \frac{k \cdot \lambda_{vac}}{\Lambda} + (\cos(\theta_{OI}))(\cos(\varphi_{OI})), \quad (4)$$

The effective index $\eta_{eff}$ may also be determined by utilizing a lookup table or model based on the optimal azimuthal angle $\phi_{OI}$. The center wavelength $\lambda_{cw}$ may then be determined from the effective index $\eta_{eff}$ as described above.

According to another embodiment, the input angle $\theta_I$ remains constant during coupling and the wavelength $\lambda_{vac}$ of the diagnostic laser beam 20 emitted by the diagnostic laser 10 is tuned. The wavelength $\lambda_{vac}$ is tuned for the maximum coupled power at a fixed input angle $\theta_I$. As the wavelength $\lambda_{vac}$ is adjusted, the intensity of the out-coupled beam (e.g., beam 27) is measured. The optimal wavelength of the diagnostic laser beam $\lambda_O$ is the wavelength $\lambda_{vac}$ that yields the highest measured intensity level of the out-coupled beam 27. The optimal wavelength $\lambda_O$ may then be used to determine the effective index $\eta_{eff}$ at the wavelength of the diagnostic laser beam 20 per equation (2) described above, or by using an appropriate lookup table or model. Similarly, the center wavelength $\lambda_{cw}$ of the waveguide region 40 may be determined per equation (3) above or appropriate lookup table or model.

Another embodiment may utilize the temperature characteristics of the non-linear optical material. With the wavelength and angle of the diagnostic beam known and fixed, the temperature of the non-linear wafer may be tuned as the power intensity of the out-coupled beam (e.g., beam 27) is measured. A look-up table based on theory or previous device characterization allows prediction of the center wavelength at the desired temperature.

The conversion efficiency of the waveguide region or regions 40 under test may also be estimated. The output detector or detectors 52 and 54 may be configured to detect the power level of a wavelength-converted out-coupled beam (e.g., green power level). The diagnostic laser 10 may be controlled to tune the wavelength of the diagnostic output beam 20 so that the converted power level may be measured for the varied wavelengths. The measured green power level at each wavelength may be plotted versus the tuned wavelength to generate an estimate of the conversion efficiency of the waveguide region 40 under test. The wavelength that provides the highest level of green power is the peak conversion wavelength. According to this embodiment, either the coupling efficiency of the diagnostic laser beam should be fairly constant over the wavelength variation, or the coupling should be continually optimized using angle or temperature adjustments.

Despite enhanced index gratings provided by the application of an electric field, some of the diagnostic laser beam 20 will not be coupled into the waveguide region 40 but rather scattered by the substrate. To enhance the sensitivity of the non-linear optical material characterizations described above, phase-sensitive detection techniques known in the art may be utilized to determine guided light versus light that is not coupled but is scattered by the substrate. Modulating the signal to the output electrodes 60a, b and 62a, b will provide for phase-sensitive detection of guided light versus scattered light.

The coupling and non-linear optical material characterization methods described above may be implemented in an automated wavelength conversion device fabrication process. Further, wafer-scale testing may be implemented into the fabrication process by using multiple input and output points on the waveguide layer of the wafer and multiple light sources tunable in angle and/or wavelength. The transfer to and from the testing station, as well as the testing procedures, may be fully automated. Undiced wafers may be assigned for further processing or rejection depending on the measurement results.

It is noted that recitations herein of a component of the present invention being "configured" in a particular way, "configured" to embody a particular property, or function in a particular manner, are structural recitations as opposed to recitations of intended use. More specifically, the references herein to the manner in which a component is "configured" denotes an existing physical condition of the component and, as such, is to be taken as a definite recitation of the structural characteristics of the component.

It is also noted that the use of the phrase "at least one" in describing a particular component or element does not imply that the use of the term "a" in describing other components or elements excludes the use of more than one for the particular component or element. More specifically, although a component may be described using "a," it is not to be interpreted as limiting the component to only one.

Having described the invention in detail and by reference to specific embodiments thereof, it will be apparent that modifications and variations are possible without departing from the scope of the invention defined in the appended claims.

More specifically, although some aspects of the present invention are identified herein as preferred or particularly advantageous, it is contemplated that the present invention is not necessarily limited to these preferred aspects of the invention.

What is claimed is:

1. A method of characterizing a non-linear optical material comprising a waveguide layer, wherein the waveguide layer comprises a plurality of periodically poled domains and at least one waveguide region, the method comprising:
coupling at least one diagnostic laser beam into the at least one waveguide region at one or more input locations positioned on the waveguide layer of the non-linear optical material;
out-coupling the diagnostic laser beam from the waveguide region at a first output location positioned on the waveguide layer of the non-linear optical material by applying an electric field to the periodically poled domains at the first output location;
measuring a first intensity level of the out-coupled beam at the first output location;
out-coupling the diagnostic laser beam from the waveguide region at a second output location positioned on the waveguide layer of the non-linear optical material by applying an electric field to the periodically poled domains at the second output location;
measuring a second intensity level of the out-coupled beam at the second output location; and
determining a propagation loss value by determining the difference between the first and second measured intensity levels.

2. A method as claimed in claim 1 wherein the electric field is applied to the periodically poled domains at the at least one or more output locations by supplying current or voltage to at least one electrode positioned at the one or more output locations.

3. A method as claimed in claim 1 wherein the method further comprises applying an electric field to the periodically poled domains at the one or more input locations by supplying current or voltage to at least one electrode positioned at the one or more input locations.

4. A method as claimed in claim 1 wherein the periodically poled domains at the input location comprise a periodicity that is different from the periodicity of a remainder of the periodically poled domains of the waveguide region.

5. A method as claimed in claim 1 wherein the non-linear optical material comprises a wafer further comprising a plurality of waveguide regions and the at least one optical property is determined for each of the plurality of waveguide regions.

6. A method as claimed in claim 1 wherein the method further comprises:
modulating the power of the electric field; and
detecting the light of the diagnostic laser beam that is guided within the waveguide region and light that is scattered off of the non-linear optical material.

7. A method of characterizing a non-linear optical material comprising a waveguide layer, wherein the waveguide layer comprises a plurality of periodically poled domains and at least one waveguide region, the method comprising:
coupling at least one diagnostic laser beam into the at least one waveguide region at one or more input locations positioned on the waveguide layer of the non-linear optical material;
out-coupling the diagnostic laser beam from the at least one waveguide region by applying an electric field to the periodically poled domains at one or more output locations positioned on the waveguide layer of the non-linear optical material;
measuring an intensity level of the out-coupled beam;
adjusting an input angle $\theta_I$, wherein the input angle $\theta_I$ is the angle of the diagnostic laser beam relative to the non-linear optical material at the input location;
determining an optimal input angle $\theta_{OI}$ based at least in part on the measured intensity level of the out-coupled beam; and
determining a center wavelength $\lambda_{cw}$ of the waveguide region based at least in part on the optimal input angle $\theta_{OI}$.

8. A method as claimed in claim 7 wherein the optimal input angle $\theta_{OI}$ is the input angle $\theta_I$ that provides for the largest measured intensity level of the out-coupled beam.

9. A method as claimed in claim 7 wherein the center wavelength $\lambda_{cw}$ of the waveguide region is determined by:

$$\lambda_{cw} = 2\Lambda(n_{eff\,2\upsilon} - n_{eff})$$

where:
$\Lambda$ is the poling period of the periodically poled domains;
k is the number of orders for coupling;
$n_{eff\,2\upsilon}$ is the effective index of the waveguide at the frequency doubled wavelength; and
$n_{eff}$ is the effective index of waveguide at the wavelength of the diagnostic laser beam.

10. A method as claimed in claim 7 wherein the input angle $\theta_I$ is adjusted by adjusting the angle of the diagnostic laser beam.

11. A method as claimed in claim 7 wherein the input angle $\theta_I$ is adjusted by tilting the non-linear optical material.

12. A method of characterizing a non-linear optical material comprising a waveguide layer, wherein the waveguide layer comprises a plurality of periodically poled domains and at least one waveguide region, the method comprising:
coupling at least one diagnostic laser beam into the at least one waveguide region at one or more input locations positioned on the waveguide layer of the non-linear optical material;
out-coupling the diagnostic laser beam from the at least one waveguide region by applying an electric field to the periodically poled domains at one or more output locations positioned on the waveguide layer of the non-linear optical material;
measuring an intensity level of the out-coupled beam;
coupling the diagnostic laser beam into the at least one waveguide region at an input angle $\theta_I$;
adjusting an azimuthal input angle $\phi_I$ of the diagnostic laser beam relative to the periodically poled domains by rotating the non-linear optical material;
determining an optimal azimuthal input angle $\phi_I$ based at least in part on the measured intensity level of the out-coupled beam; and
determining a center wavelength $\lambda_{cw}$ of the waveguide region based at least in part on the input angle $\theta_I$ and the best azimuth input angle $\phi_{OI}$.

13. A method of characterizing a non-linear optical material comprising a waveguide layer, wherein the waveguide layer comprises a plurality of periodically poled domains and at least one waveguide region, the method comprising:
coupling at least one diagnostic laser beam into the at least one waveguide region at one or more input locations positioned on the waveguide layer of the non-linear optical material;
out-coupling the diagnostic laser beam from the at least one waveguide region by applying an electric field to the periodically poled domains at one or more output locations positioned on the waveguide layer of the non-linear optical material;

measuring an intensity level of the out-coupled beam;

adjusting the wavelength of the diagnostic laser beam;

determining an optimal wavelength of the diagnostic laser beam $\lambda_O$ based at least in part on the measured intensity level of the out-coupled beam; and determining a center wavelength $\lambda_{cw}$ of the waveguide region based at least in part on the optimal wavelength $\lambda_O$.

14. A method as claimed in claim 13 wherein the optimal wavelength $\lambda_O$ is the wavelength of the diagnostic laser beam that provides for the largest measured intensity level of the out-coupled beam.

15. A method of characterizing a non-linear optical material comprising a waveguide layer, wherein the waveguide layer comprises a plurality of periodically poled domains and at least one waveguide region, the method comprising:

coupling at least one diagnostic laser beam into the at least one waveguide region at one or more input locations positioned on the waveguide layer of the non-linear optical material;

out-coupling the diagnostic laser beam from the at least one waveguide region by applying an electric field to the periodically poled domains at one or more output locations positioned on the waveguide layer of the non-linear optical material;

measuring an intensity level of the out-coupled beam;

coupling the diagnostic laser beam into the at least one waveguide region at an input angle $\theta_f$;

adjusting a temperature of the non-linear optical material;

determining an optimal temperature of the non-linear optical material based at least in part on the measured intensity level of the out-coupled beam; and determining a center wavelength $\lambda_{cw}$, of the waveguide region at the optimal temperature.

16. A method of characterizing a non-linear optical material comprising a waveguide layer, wherein the waveguide layer comprises a plurality of periodically poled domains and at least one waveguide region, the method comprising:

coupling at least one diagnostic laser beam into the at least one waveguide region at one or more input locations positioned on the waveguide layer of the non-linear optical material;

out-coupling the diagnostic laser beam from the at least one waveguide region by applying an electric field to the periodically poled domains at one or more output locations positioned on the waveguide layer of the non-linear optical material;

adjusting the frequency of the diagnostic laser beam;

measuring a green power intensity level of the out-coupled beam;

determining an optimal frequency of the diagnostic laser beam based at least in part on the measured green power intensity level of the out-coupled beam; and determining the conversion efficiency of the waveguide region based at least in part on the optimal frequency of the diagnostic laser beam.

* * * * *